US011198657B2

(12) United States Patent
Suzuki et al.

(10) Patent No.: US 11,198,657 B2
(45) Date of Patent: Dec. 14, 2021

(54) METHOD FOR PRODUCING CONJUGATED DIENE

(71) Applicant: KURARAY CO., LTD., Kurashiki (JP)

(72) Inventors: Yutaka Suzuki, Kamisu (JP); Masaki Shimizu, Chiyoda-ku (JP)

(73) Assignee: KURARAY CO., LTD., Kurashiki (JP)

( * ) Notice: Subject to any disclaimer, the term of this patent is extended or adjusted under 35 U.S.C. 154(b) by 0 days.

(21) Appl. No.: 15/577,988

(22) PCT Filed: Jun. 1, 2016

(86) PCT No.: PCT/JP2016/066297
§ 371 (c)(1),
(2) Date: Nov. 29, 2017

(87) PCT Pub. No.: WO2016/194983
PCT Pub. Date: Dec. 8, 2016

(65) Prior Publication Data
US 2018/0290947 A1 Oct. 11, 2018

(30) Foreign Application Priority Data
Jun. 3, 2015 (JP) .............................. JP2015-113006

(51) Int. Cl.
*C07C 1/24* (2006.01)
*C07C 29/44* (2006.01)
*C07C 29/38* (2006.01)
*C07C 11/18* (2006.01)

(52) U.S. Cl.
CPC ................ *C07C 1/24* (2013.01); *C07C 29/38* (2013.01); *C07C 29/44* (2013.01); *C07C 11/18* (2013.01); *C07C 2527/173* (2013.01)

(58) Field of Classification Search
None
See application file for complete search history.

(56) References Cited

U.S. PATENT DOCUMENTS

| 2,626,284 | A | * | 1/1953 | Smith | .................... C07C 29/74 568/919 |
| 3,657,376 | A | | 4/1972 | Stuebinger et al. | |
| 3,714,285 | A | | 1/1973 | Mueller et al. | |
| 3,778,479 | A | * | 12/1973 | Morrisroe | ............. C07C 29/095 510/235 |
| 3,993,702 | A | | 11/1976 | Hawkins | |
| 4,028,424 | A | * | 6/1977 | Yoshida | .................. C07C 29/38 568/879 |
| 4,381,416 | A | * | 4/1983 | Kyo | .......................... C07C 1/20 585/606 |
| 4,511,751 | A | | 4/1985 | Ninagawa et al. | |
| 7,442,844 | B2 | | 10/2008 | Yamada et al. | |

FOREIGN PATENT DOCUMENTS

| CN | 102206136 A | 10/2011 |
| CN | 102516009 A | 6/2012 |
| CN | 103224444 A | 7/2013 |
| DE | 1 275 049 B | 8/1968 |
| DE | 2 116 948 A1 | 10/1972 |
| GB | 1 205 397 A | 9/1970 |
| GB | 1344713 | 1/1974 |
| GB | 1 528 876 A | 10/1978 |
| JP | 47-1571 A | 1/1972 |
| JP | 47-1714 | 1/1972 |
| JP | 47-14105 | 8/1972 |
| JP | 50-1003 B | 1/1975 |
| JP | 59-184137 A | 10/1984 |
| JP | 7-285899 A | 10/1995 |
| JP | 2013-75877 A | 4/2013 |
| WO | 2004/087625 A1 | 10/2004 |
| WO | 2015/186699 A1 | 12/2015 |

OTHER PUBLICATIONS

Machine translation JP 47-014105 A. Jan. 1972. (Year: 1972).*
Machine translation DE 1275049 dated Aug. 14, 1968. Accessed Dec. 31, 2019 (Year: 2019).*
International Search Report dated Jul. 26, 2016 in PCT/JP2016/066297 Filed Jun. 1, 2016.
Combined Singaporean Search Report and Written Opinion dated Oct. 25, 2018 in Singaporean Patent Application No. 11201709802X, 9 pages.
Extended European Search Report dated Dec. 11, 2018 in Patent Application No. 16803417.1, 6 pages.
Office Action dated Oct. 1, 2019, in Russian Patent Application No. 2017146189 filed Jun. 1, 2016 (with English translation).
Written Opinion dated Nov. 5, 2019, in Singaporean Patent Application No. 11201709802X filed Jun. 1, 2016.
S.Yu. Pavlov et al., "Perspektivi razvitia proizvodstva kauchuka", Khimitshcheskaya promishlennost, No. 7, 12(466)-19(473) (1997).
Combined Chinese Office Action and Search Report dated Jan. 21, 2021 in Patent Application No. 201680031521.0 (English translation of Category of Cited Documents), 7 pages.

\* cited by examiner

*Primary Examiner* — Philip Y Louie
*Assistant Examiner* — Alyssa L Cepluch
(74) *Attorney, Agent, or Firm* — Oblon, McClelland, Maier & Neustadt, L.L.P.

(57) ABSTRACT

A method for producing a conjugated diene, including a step A of allowing an α-olefin and formaldehyde to react with each other to produce a γ,δ-unsaturated alcohol in the presence of an alcohol; and a step B of subjecting the γ,δ-unsaturated alcohol to a dehydration reaction at 135 to 210° C. in the presence of an aqueous solution of an acidic catalyst.

9 Claims, No Drawings

METHOD FOR PRODUCING CONJUGATED DIENE

TECHNICAL FIELD

The present invention relates to a method for producing a conjugated diene by producing a γ,δ-unsaturated alcohol from an α-olefin and formaldehyde and subjecting the resulting γ,δ-unsaturated alcohol to a dehydration reaction.

BACKGROUND ART

As one of production methods of a conjugated diene, there is exemplified a method for synthesizing it through a one-stage reaction from an α-olefin and formaldehyde. For example, there is known a production method of isoprene by feeding isobutene, formaldehyde, and water continuously or intermittently into an acidic aqueous solution and undergoing a reaction while distilling produced isoprene outside the reaction system (see PTL 1). But, this production method involves such problems that a selectivity of isoprene is low as about 73%; and that the production amount of high boiling point byproducts is high.

With respect to the selectivity, there would be a possibility that by dividing the reaction into plural stages each having a high selectivity, the total selectivity is improved as compared with that in the case of synthesis through a one-stage reaction. For example, when a γ,δ-unsaturated alcohol is produced from an α-olefin and formaldehyde and subjecting the resulting γ,δ-unsaturated alcohol to a dehydration reaction to produce a conjugated diene, the reaction becomes a two-stage reaction; and in this case, if the selectivity of each reaction is high, there would be a possibility that the resulting selectivity is higher than that when produced by the one-stage reaction.

As the method for producing the γ,δ-unsaturated alcohol from an α-olefin and formaldehyde, there is disclosed a method in which the reaction between the α-olefin and formaldehyde is carried out using, as a solvent, an alcohol having a carbon number of 3 to 10 in the absence of a catalyst at 150 to 350° C. and at 30 to 500 atms (see PTL 2). According to this method, 3-methyl-3-buten-1-ol is obtained at a selectivity of about 91% at maximum.

Meanwhile, with respect to the dehydration reaction of the γ,δ-unsaturated alcohol, there is, for example, disclosed a method in which 3-methyl-3-buten-1-ol is subjected to vapor phase dehydration in the presence of a catalyst of phosphoric acid supported on pumice or calcium phosphate (see PTLs 3 and 4). According to such a method, in order to vaporize the raw material, it is necessary to perform the reaction at high temperatures, or to vaporize the raw material under a reduced pressure under certain circumstances. In all of the cases, in order to vaporize the raw material, there is involved such an economic disadvantage that a large quantity of heat source must be used, or there would also be a concern about decomposition of the γ,δ-unsaturated alcohol heated at high temperatures.

As a method for solving these problems, there is exemplified a method in which a dehydration reaction is performed in a liquid phase system of a lower reaction temperature. As such a method, there is disclosed a method in which isoprene monool or an acid ester thereof is allowed to react in a liquid phase under pressure at a reaction temperature of 100 to 180° C. in the presence of a catalyst, and specifically, there is described an example of using 3-methyl-3-buten-1-ol (see PTL 5). But, not only PTL 5 does not describe at all the industrial and continuous reaction method, but also PTL 5 describes the method in which a glass tube having the catalyst sealed therein is broken to commence the reaction at the same time of commencement of stirring, and therefore, the disclosed method cannot be immediately applied from the industrial viewpoint.

CITATION LIST

Patent Literature

PTL 1: WO 2004/087625 A
PTL 2: JP 7-285899 A
PTL 3: JP 47-1571 A
PTL 4: JP 50-1003 B
PTL 5: JP 47-14105 A

SUMMARY OF INVENTION

Technical Problem

A problem of the present invention is to provide a method for producing a conjugated diene industrially stably at a high selectivity.

Solution to Problem

As a result of extensive and intensive investigations made by the present inventors, it has been found that when the γ,δ-unsaturated alcohol obtained by allowing an α-olefin and formaldehyde to react with each other is subjected to a dehydration reaction at a high temperature in the presence of an acidic catalyst, the selectivity of the conjugated diene can be stably enhanced, thereby leading to accomplishment of the present invention.

Specifically, the present invention provides the following [1] to [8].

[1] A production method of a conjugated diene, including a step A of allowing an α-olefin and formaldehyde to react with each other to produce a γ,δ-unsaturated alcohol; and a step B of subjecting the γ,δ-unsaturated alcohol to a dehydration reaction at 135 to 210° C. in the presence of an aqueous solution of an acidic catalyst.

[2] The production method of [1], wherein in the step A, a solvent is allowed to coexist.

[3] The production method of [2], wherein the solvent is an alcohol.

[4] The production method of any of [1] to [3], wherein the α-olefin is isobutene, and the γ,δ-unsaturated alcohol is 3-methyl-3-buten-1-ol.

[5] The production method of any of [1] to [4], wherein the step B includes feeding the γ,δ-unsaturated alcohol and water continuously or intermittently into a reactor; and taking the produced conjugated diene and water continuously or intermittently out of the reaction system.

[6] The production method of [5], wherein {(feed rate of water (mol/hr))/(feed rate of γ,δ-unsaturated alcohol (mol/hr))} is from 0.5 to 12.

[7] The production method of any of [1] to [6], wherein the acidic catalyst is phosphoric acid.

[8] The production method of any of [1] to [7], wherein a reaction pressure in the dehydration reaction is from 0.35 to 1.6 MPa.

Advantageous Effects of Invention

In accordance with the production method of the present invention, it is possible to provide a method for producing a conjugated diene industrially stably at a high selectivity.

DESCRIPTION OF EMBODIMENTS

The production method of a conjugated diene of the present invention includes a step of producing a γ,δ-unsaturated alcohol from an α-olefin and formaldehyde (this step will be hereinafter referred to as "step A"); and a step of subjecting the γ,δ-unsaturated alcohol obtained in the step A to a dehydration reaction in the presence of an acidic catalyst (this step will be hereinafter referred to as "step B").

[Step A]

The step A is a step of allowing an α-olefin represented by the following general formula (I) (hereinafter referred to as "α-olefin (I)"):

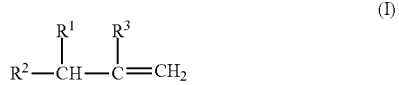
(I)

(in the formula, $R^1$, $R^2$, and $R^3$ each independently represent a hydrogen atom or an alkyl group having a carbon number of 1 to 10, and $R^1$ and $R^3$ may be connected to each other to form a ring)
and formaldehyde to react with each other, to produce a γ,δ-unsaturated alcohol represented by the following general formula (II):

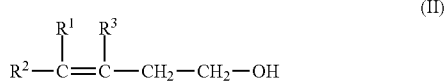
(II)

(in the formula, $R^1$, $R^2$, and $R^3$ are the same as defined above).

(α-Olefin (I))

Examples of the alkyl group having a carbon number of 1 to 10, which $R^1$, $R^2$, and $R^3$ each independently represent, include a methyl group, an ethyl group, various propyl groups (it is expressed by the term "various" that linear and all branched groups are included; hereinafter the same), various butyl groups, various hexyl groups, various octyl groups, various decyl groups, and the like. Above all, an alkyl group having a carbon number of 1 to 5 is preferred, an alkyl group having a carbon number of 1 to 3 is more preferred, and a methyl group is still more preferred. As the ring in the case where $R^1$ and $R^3$ are connected to each other to form a ring, a saturated aliphatic ring having a carbon number of 5 to 10, such as a cyclopentane ring, a cyclohexane ring, a cyclooctane ring, etc., is preferred, and a cyclohexane ring is more preferred.

With respect to $R^1$, $R^2$, and $R^3$, it is yet still more preferred that at least one of $R^1$ and $R^2$ is a hydrogen atom, and $R^3$ is an alkyl group having a carbon number of 1 to 10; and it is especially preferred that all of $R^1$ and $R^2$ are a hydrogen atom, and $R^3$ is an alkyl group having a carbon number of 1 to 10. More preferred examples of the alkyl group are the same as described above.

Specific examples of the α-olefin (I) include:
(1) propylene in which all of $R^1$, $R^2$, and $R^3$ are a hydrogen atom;
(2) isobutene, as an example of the α-olefin (I) in which $R^1$ and $R^2$ are a hydrogen atom, and $R^3$ is an alkyl group having a carbon number of 1 to 10;
(3) 2-methyl-1-butene, 2-methyl-1-pentene, 2-methyl-1-hexene, 2-methyl-1-heptene, or 2-methyl-1-octene, as an example of the α-olefin (I) in which at least one of $R^1$ and $R^2$ is a hydrogen atom, and $R^3$ is an alkyl group having a carbon number of 1 to 10;
(4) 2,3-dimethyl-1-butene, as an example of the α-olefin (I) in which all of $R^1$, $R^2$, and $R^3$ are an alkyl group having a carbon number of 1 to 10; and
(5) methylenecyclohexane or the like, as an example of the α-olefin (I) in which $R^2$ is a hydrogen atom, and $R^1$ and $R^3$ are connected to each other to form a ring.

The use amount of the α-olefin (I) in the step A is preferably 1 to 50 mol, more preferably 3 to 30 mol, and still more preferably 3 to 20 mol per mol of formaldehyde. When the use amount of the α-olefin (I) is 1 mol or more per mol of formaldehyde, the selectivity of the desired γ,δ-unsaturated alcohol is improved; whereas it is 50 mol or less, not only the equipment required for recovery of the α-olefin (I) becomes small, so that an industrial value is improved, but also the volume efficiency is improved, and the productivity is improved.

(Formaldehyde)

In the step A, formaldehyde may be used as it is, or may also be used upon being dissolved in a solvent. Although the solvent that dissolves formaldehyde therein is not particularly limited, the solvent is preferably water from the standpoint of easiness of availability, namely it is preferred to use a formaldehyde aqueous solution. In this case, from the viewpoint of volume efficiency, it is preferred that the concentration of formaldehyde is high; however, when the concentration is excessively high, a problem of deposition is generated to make handling difficult, so that the concentration of formaldehyde of the formaldehyde solution is typically 10 to 70% by mass, and preferably 30 to 60% by mass.

(Solvent)

Although the reaction of the step A may be carried out in the presence or absence of a solvent, it is preferred to carry out the reaction in the presence of a solvent. The solvent is not particularly limited so long as it does not adversely affect the reaction, and examples thereof include organic solvents, such as aliphatic hydrocarbons, e.g., pentane, hexane, heptane, octane, nonane, decane, cyclohexane, cyclooctane, etc.; aromatic hydrocarbons, e.g., benzene, toluene, xylene, mesitylene, etc.; alcohols, e.g., methanol, ethanol, tert-butyl alcohol, etc.; ethers, e.g., diethyl ether, diisopropyl ether, tetrahydrofuran, etc.; etc.

In the case of using the aforementioned formaldehyde as an aqueous solution, the solvent is preferably an alcohol, and more preferably an alcohol having a carbon number of 3 to 10. Examples of the alcohol having a carbon number of 3 to 10 include, but not limited to, aliphatic alcohols, such as n-propanol, isopropanol, n-butanol, tert-butyl alcohol, isobutanol, sec-butyl alcohol, n-amyl alcohol, isoamyl alcohol, tert-amyl alcohol, hexanol, 2-methyl-2-butanol, 3-methyl-3-pentanol, 2-ethylhexanol, heptanol, octanol, nonanol, etc.; alicyclic alcohols, such as cyclohexanol, methylcyclohexanol, cyclopentanol, etc.; aromatic alcohols, such as benzyl alcohol, etc.; and the like. Among those, from the viewpoint of uniformly dissolving the α-olefin (I) and formaldehyde, isopropanol, isobutanol, sec-butyl alcohol, tert-butyl alcohol, isoamyl alcohol, or tert-amyl alcohol is preferred, and tert-butyl alcohol is more preferred.

The solvent may be used either alone or in combination of two or more thereof. In addition, other solvent may also be used in combination so long as it does not adversely affect the present reaction.

The use amount of the solvent is preferably 0.5 to 20 mol, and more preferably 1 to 10 mol per mol of formaldehyde. When the use amount of the solvent is 0.5 mol or more per mol of formaldehyde, by production of an alkyl-m-dioxane may be suppressed; whereas when it is 20 mol or less, the size of distillation equipment for undergoing separation and recovery as well as the use amount of steam working as a heat source, an electric power, or the like may be simplified, so that an industrial value is improved.

(Reaction Conditions, Etc.)

The reaction temperature in the step A is preferably 150 to 350° C., more preferably 200 to 330° C., and still more preferably 240 to 310° C. When the reaction temperature is 150° C. or higher, the reaction rate is large, so that the reaction time may be shortened; whereas when it is 350° C. or lower, the decomposition reaction of formaldehyde and the produced γ,δ-unsaturated alcohol is suppressed, and the yield of the desired γ,δ-unsaturated alcohol is improved.

While the reaction time is suitably determined by the reaction temperature, the reaction is typically completed for 1 minute to 30 minutes. Accordingly, even in the case of undergoing the reaction in a continuous mode as described later, the retention time within a reaction tube may be 1 minute to 30 minutes.

The reaction pressure in the step A may be typically a distillation pressure at the reaction temperature of the α-olefin (I) or higher. In the case of using the α-olefin (I) exceeding critical conditions at a predetermined temperature, it is recommended to control the pressure as needed. The reaction pressure is preferably 3 to 50 MPa, more preferably 3 to 30 MPa, still more preferably 5 to 30 MPa, and especially preferably 10 to 30 MPa. When the reaction pressure is a distillation pressure at a predetermined temperature of the α-olefin (I) or higher, the concentration of the α-olefin (I) in the reaction liquid becomes high, thereby bringing about improvements in the reaction rate and the selectivity of the γ,δ-unsaturated alcohol. In addition, when the reaction pressure is controlled to 50 MPa or less, a construction cost of the pressure-resistant equipment is suppressed, and a risk of rapture of the reaction apparatus is also lowered.

In the step A, it is preferred to use a reactor capable of controlling the aforementioned reaction temperature, reaction time, and reaction pressure. In addition, the reaction of the step A may be carried out by any method of batch, semi-batch, and continuous modes. Above all, it is preferred to undergo the reaction in a continuous mode in which the conversion of formaldehyde and the selectivity and yield of the γ,δ-unsaturated alcohol become high.

A specific and preferred embodiment in the case of undergoing the reaction in a continuous mode is as follows. A mixed solution containing the α-olefin (I), the formaldehyde aqueous solution, and the solvent is fed at a desired flow rate into the reaction tube heated at a predetermined temperature. The reaction pressure is adjusted so as to keep an outlet of a condenser tube connected to an outlet of the reaction tube at a predetermined pressure, the aforementioned mixed solution is retained within the reaction tube for a predetermined time, and the reaction is performed while flowing out the reaction liquid from the outlet of the reaction tube. In the case where the α-olefin (I) remains in the resulting reaction liquid, it is preferred to fractionate the α-olefin (I) and again use it as the raw material.

[Step A' (Washing)]

The production method of the present invention may include, after the step A, a step of washing the resulting reaction liquid (step A'). Although the washing method in the step A' is not particularly limited, it is preferred to undergo alkali washing including a step of bringing the reaction liquid into contact with an alkaline aqueous solution. When the resulting reaction liquid is brought into contact with the alkaline aqueous solution and then separated, the removal of formic acid and a formic acid ester generated as byproducts and the improvement in yield of the γ,δ-unsaturated alcohol may be achieved at the same time. It may be conjectured that this is caused due to the matters that all of the formic acid and formic acid ester in the resulting reaction liquid are converted to a formate and removed, whereby the purity of the γ,δ-unsaturated alcohol is increased; and that since the formic acid ester in the reaction liquid is a condensate of formic acid and the γ,δ-unsaturated alcohol, the desired γ,δ-unsaturated alcohol is formed by decomposition. It has become clear that as for formic acid, on the occasion of purification by distillation, the γ,δ-unsaturated alcohol is liable to be converted to a high boiling point compound due to the presence thereof; and that it is difficult to separate the formic acid ester from the γ,δ-unsaturated alcohol by means of distillation, and therefore, the matter that the mixed amount of the formic acid and formic acid ester may be thoroughly decreased by the present step is quite meaningful.

The method for bringing the reaction liquid into contact with the alkaline aqueous solution is not particularly limited, and for example, (i) a method in which the reaction liquid and the alkaline aqueous solution are introduced into a vessel equipped with a stirrer, and the both are stirred (batch mode); (ii) a method in which the reaction liquid and the alkaline aqueous solution are brought into continuous contact with each other in a counter current mode (preferably a complete counter current mode) (continuous mode); and the like may be adopted.

As the alkali, it is preferred to use at least one selected from an alkali metal hydroxide, an alkali metal carbonate, an alkali metal acetate, an alkali metal phosphate, an alkaline earth metal hydroxide, an alkaline earth metal carbonate, an alkaline earth metal acetate, and an alkaline earth metal phosphate. Above all, from the viewpoints of easiness of availability, removal efficiency of the formic acid and formic acid ester, and selectivity and yield of the γ,δ-unsaturated alcohol, sodium hydroxide, potassium hydroxide, sodium carbonate, or potassium carbonate is preferred, and sodium hydroxide is more preferred.

The alkali may be used either alone or in combination of two or more thereof.

In the case of undergoing the alkali washing in the step A', from the viewpoints of removal efficiency of the formic acid and formic acid ester and selectivity and yield of the γ,δ-unsaturated alcohol, an "aqueous solution" of the alkali is used. Although the concentration of the alkali in the alkaline aqueous solution is not particularly limited, from the viewpoint of easiness of handling as well as the viewpoints of removal efficiency of the formic acid and formic acid ester and selectivity and yield of the γ,δ-unsaturated alcohol, the concentration is preferably 0.01 to 20 mol/L, more preferably 0.1 to 20 mol/L, still more preferably 0.1 to 10 mol/L, and especially preferably 0.1 to 5 mol/L. By bringing such an alkaline aqueous solution into contact with the aforementioned reaction liquid, the pH of the aqueous solution in the resulting solution is controlled to 9 to 13. The pH is adjusted to preferably 10 to 13, more preferably 11 to 13, and still more preferably 12 to 13. In this way, as for the pH of the aqueous solution in the solution obtained by bringing the alkaline aqueous solution and the aforementioned reaction liquid into contact with each other, from the viewpoints of removal efficiency of the formic acid and formic acid ester and selectivity and yield of the γ,δ-unsaturated alcohol, a pH of less than 9 is insufficient, and the aqueous solution is required to exhibit alkalinity stronger than that.

Although the temperature at which the reaction liquid and the alkaline aqueous solution are brought into contact with each other is not particularly limited, from the viewpoints of removal efficiency of the formic acid and formic acid ester and selectivity and yield of the γ,δ-unsaturated alcohol, it is preferably 10 to 90° C., more preferably 20 to 90° C., still more preferably 35 to 85° C., and especially preferably 50 to 80° C.

As for the contact time between the reaction liquid and the alkaline aqueous solution, though any length may be adopted so long as it is possible to sufficiently remove the formic acid and formic acid-derived ester in the raw material liquid, the contact time is preferably 2 minutes to 600 minutes, and more preferably 5 minutes to 500 minutes. In the case of adopting the aforementioned complete counter current mode, it is preferred to adjust the contact time such that the time of retaining within a column is 2 minutes to 600 minutes (preferably 5 minutes to 500 minutes, and more preferably 30 minutes to 500 minutes).

In the reaction liquid having gone through the alkali washing, the content of formic acid as an impurity is extremely low. Therefore, not only there is no risk of corrosion of the apparatus by formic acid, but also for example, on the occasion of purification by distillation, there is no concern that the γ,δ-unsaturated alcohol is converted to a high boiling point compound due to formic acid, so that the yield may be maintained high.

(Purification)

After the step A and optionally, the step A', the γ,δ-unsaturated alcohol with a higher purity is obtained through purification.

The purification method is not particularly limited, and though after fractionating the organic layer, the purification may be performed by means of column chromatography or the like, in the case of carrying out the purification industrially continuously, purification by distillation is preferred. In the case of undergoing the purification by distillation, the theoretical plate number of a distillation column is preferably 10 to 60, more preferably 10 to 40, and still more preferably 10 to 30. In addition, the reflux ratio is preferably 0.5 to 1.5, and more preferably 0.7 to 1.2. Although the heating temperature and the pressure on the occasion of purification by distillation are not particularly limited, for example, it is preferred to undergo the purification by distillation at 100 to 180° C. and at 3 to 10 kPa, and it is more preferred to undergo the purification by distillation at 120 to 160° C. and at 3 to 7 kPa.

As for the purification by distillation, the γ,δ-unsaturated alcohol with a high purity may be obtained through a one-time distillation operation using a single distillation column; or the distillation may be achieved dividedly two or more times by plural distillation operations using two or more distillation columns, thereby separating impurities stepwise and increasing the purity of the γ,δ-unsaturated alcohol step-by-step.

[Step B]

The step B is a step of dehydrating the γ,δ-unsaturated alcohol obtained by the step A and optionally, the step A' in the presence of an acidic catalyst, to produce a conjugated diene represented by the following general formula (III):

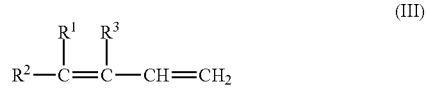

(in the formula, $R^1$, $R^2$, and $R^3$ are the same as defined above).

(Acidic Catalyst)

Examples of the acidic catalyst include phosphoric acid, phosphorous acid, nitric acid, sulfuric acid, hydrogen chloride, hydrogen bromide, hydrogen fluoride, hypochlorous acid, chlorous acid, chloric acid, perchloric acid, boric acid, fluorosulfonic acid, benzenesulfonic acid, p-toluenesulfonic acid, methanesulfonic acid, trifluoromethanesulfonic acid, trifluoroacetic acid, oxalic acid, and the like. Above all, from the viewpoint of selectivity of the conjugated diene, phosphoric acid, sulfuric acid, boric acid, p-toluenesulfonic acid, or methanesulfonic acid is preferred, and phosphoric acid is more preferred.

From the viewpoint of suppressing the generation of high boiling point byproducts within the reaction system, it is preferred that the acidic catalyst is used as an aqueous solution. The concentration of the acidic catalyst within the reaction system is preferably 0.2 to 10% by mass, more preferably 0.5 to 8% by mass, still more preferably 1 to 5% by mass, and yet still more preferably 1 to 4% by mass. When the concentration of the acidic catalyst within the reaction system falls within this range, the production of high boiling point byproducts is suppressed, the selectivity of the conjugated diene may be enhanced, and the conversion of the γ,δ-unsaturated alcohol may also be maintained high. In general, it is preferred to charge the acidic catalyst aqueous solution into the reactor before commencement of the reaction, and it is preferred that the concentration of the acidic catalyst of the acidic catalyst aqueous solution at that time falls within the aforementioned range.

(Water)

In the reaction in the step B, it is preferred to feed water together with the γ,δ-unsaturated alcohol into the reactor. According to this, fluctuation in concentration of the acidic catalyst within the reaction system may be suppressed, and at the same time, the pressure within the reaction system may be easily maintained at a fixed value. From the viewpoint of producing the conjugated diene industrially stably, it is preferred to adjust the feed rate of water into the reactor such that it is a ratio of a fixed range relative to the feed rate of the γ,δ-unsaturated alcohol. From this viewpoint, {(feed rate of water (mol/hr))/(feed rate of γ,δ-unsaturated alcohol (mol/hr))} is typically 0.8 to 12, preferably 0.8 to 10, more preferably 0.9 to 9, still more preferably 1 to 8, especially preferably 2 to 7, and most preferably 4 to 6.

The water to be used is not particularly limited, and for example, ion-exchanged water or distilled water may be suitably used. In addition, water produced through the reaction may be recovered and used.

(Reaction Conditions, Etc.)

The reaction temperature in the step B is 135 to 210° C. When the reaction temperature is 135° C. or higher, the reaction rate is large, so that the conjugated diene may be obtained at a high selectivity; whereas when it is 210° C. or lower, the side-reaction of the produced conjugated diene is suppressed, thereby preventing a lowering of the yield from occurring, and the use amount of a heat source may be suppressed, so that the industrial value is improved. The reaction temperature is preferably 135 to 200° C., and more preferably 135 to 195° C.

In order to keep the reaction temperature in the aforementioned high temperature state, the reaction pressure is typically controlled to 0.35 to 1.6 MPa. The reaction pressure is preferably 0.5 to 1.4 MPa, more preferably 0.5 to 1.2 MPa, and still more preferably 0.5 to 1.0 MPa. When the reaction pressure is less than 0.35 MPa, it is difficult to control the reaction temperature to 135° C. or higher.

It is preferred to carry out the reaction in the step B in an inert gas atmosphere of nitrogen, argon, or the like, and it is preferred to pressurize the inside of the reaction system with an inert gas to some extent. When the reaction commences, the pressure within the reactor is continued to be increased due to influences of the produced conjugated diene and water. Then, the reaction pressure is adjusted so as to fall within the aforementioned range by properly releasing the gas.

In the step B, from the viewpoint of making the reaction pressure and the reaction results stable, it is preferred that not only the γ,δ-unsaturated alcohol and water are continuously fed at the aforementioned predetermined ratio into the reactor, but also the produced conjugated diene and water are continuously distilled out the reaction system. Although the water includes (i) water of the acidic catalyst aqueous solution, (ii) water generated due to the dehydration reaction, (iii) water to be fed into the reactor together with the γ,δ-unsaturated alcohol, and (iv) water to be distilled from the reactor, from the viewpoint of making the reaction results stable, it is preferred to adjust various reaction conditions such that the amount of water within the reaction system is always substantially constant.

The pressure within the reactor may be kept at a predetermined value by adjusting the pressure in such a manner that at the time of commencement of the reaction, the inside of the reaction system is hermetically sealed until the pressure within the reactor reaches a predetermined value, and at a point of time of reaching the desired pressure, the gas (gas containing nitrogen, the conjugated diene, and water vapor) is released outside the reaction system so as to keep the pressure.

A total distillation rate of the conjugated diene and water distilled from the reactor (the distillation rate is a value as expressed into a liquid material obtained by cooling after distillation) is preferably 0.8 to 1.2 times by mass, and more preferably 0.9 to 1.1 times by mass of a total feed rate of the γ,δ-unsaturated alcohol and water to be fed into the reactor.

EXAMPLES

The present invention is hereunder described in more detail by reference to the following Examples, but it should be construed that the present invention is by no means limited by the these Examples.

In each of the Examples, the gas chromatography analysis was carried out under the following conditions.
[Gas Chromatography Analysis Conditions]
Analytical instrument: GC14A (manufactured by Shimadzu Corporation)
Detector: FID (flame ionization detector)
Column used: DB-1 (30 m, film thickness: 5 μm) (manufactured by J&W Scientific)
Analysis conditions: Injection inlet temperature: 280° C., detector temperature: 280° C.
Temperature rise conditions: <γ,δ-Unsaturated alcohol>70° C. (kept for 0 minute)→(temperature raised at 5° C./min)→250° C. (kept for 4 minutes), <Conjugated diene>40° C. (kept for 10 minutes)→(temperature raised at 5° C./min)→250° C. (kept for 4 minutes)

<Example 1>
[Step A]
Into a stainless steel-made reaction tube having an inside diameter of 2 mm and a length of 3,180 mm (internal volume: 10 mL) as heated at 280° C., a mixed solution of 2.4% by mass of formaldehyde, 2.4% by mass of water, 66.1% by mass of isobutene, and 29.1% by mass of tert-butyl alcohol (organic solvent) was fed at a rate of 1 mL/min. Here, an isobutene/tert-butyl alcohol/formaldehyde ratio (molar ratio) in the mixed solution is 15/5/1, and a retention time of the mixed solution is 10 minutes. An outlet of the reaction tube was connected to a condenser tube having an inside diameter of 2 mm and a length of 2,000 mm, and the reaction liquid was allowed to flow out while keeping an outlet pressure of the condenser tube at 20 MPa.

The resulting reaction liquid was analyzed by means of gas chromatography. As a result, the conversion of formaldehyde was 81.6%, and the selectivity of 3-methyl-3-buten-1-ol was 90.5%. In addition, the contents of formic acid and a formic acid ester as byproducts were 1.4% and 0.8%, respectively.

[Step A']
To 100 g of the reaction liquid obtained in the step A, a 1 mol/L sodium hydroxide aqueous solution was added in an amount of 12 mL (corresponding to 12 mmol of sodium hydroxide), and the mixture was stirred at 70° C. for 5 minutes. An organic layer (upper layer) was subjected to a gas chromatography analysis. As a result, all of formic acid and a formic acid ester of 3-methyl-3-buten-1-ol did not retain in the organic layer.

An organic layer (upper layer) after alkali washing was subjected to purification by distillation under conditions of a theoretical plate number of 20, a reflux ratio of 1, a bath temperature of 140° C., and a pressure of 5.3 kPa. As a result, 3-methyl-3-buten-1-ol having a purity of 99.4% by mass was obtained at a distillation yield of 95.0%.

[Step B]
300 g of a 1.8% by mass phosphoric acid aqueous solution was charged in a Hastelloy-made 500-mL autoclave; the inside of the autoclave was purged with nitrogen and then pressurized with nitrogen to 0.7 MPa; and heating and stirring (1,000 times/min) were commenced. When the inner temperature reached 170° C., 75.9 g/hr of 3-methyl-3-buten-1-ol obtained in the step A' and 79.4 g/hr of water [water/3-methyl-3-buten-1-ol=5.0/1.0 (molar ratio)] were fed into the autoclave.

When the internal pressure reached 0.85 MPa, release of the gas within the autoclave was commenced so as to keep the foregoing pressure. The released gas was continuously cooled by a condenser attached to the autoclave, to coagulate the reaction product, and the operation was continued for 4 hours while receiving the reaction product in a tank.

As a result of analyzing the organic layer within the tank and the reaction liquid within the reactor by means of gas chromatography, the conversion of 3-methyl-3-buten-1-ol was 98.2%, and the selectivity of isoprene was 93.1%. In addition, the selectivities of isobutene, 2-methyl-3-buten-2-ol, 3-methyl-1,3-butanediol, methyl isopropyl ketone, and an isoprene dimer, all of which are byproducts, were 1.9%, 0.6%, 0.3%, 0.9%, and 2.8%, respectively. The results are shown in Table 1.

<Examples 2 to 7 and Comparative Example 1>
The same operations were followed, except that in the step B of Example 1, the phosphoric acid concentration, the reaction temperature, the reaction pressure, the ratio of water to 3-methyl-3-buten-1-ol, and the feed rates of 3-methyl-3-buten-1-ol and water were changed as shown in Table 1. The results are shown in Table 1.

TABLE 1

| | | | Example | | | | | | | Comparative |
|---|---|---|---|---|---|---|---|---|---|---|
| | | | 1 | 2 | 3 | 4 | 5 | 6 | 7 | Example 1 |
| Reaction conditions | Acidic catalyst | Phosphoric acid concentration (% by mass) | 1.8 | 1.8 | 1.8 | 2.8 | 4.5 | 1.8 | 1.8 | 1.8 |
| | | Use amount (g) | 300 | 300 | 300 | 300 | 300 | 300 | 300 | 300 |
| | Water/3-methyl-3-buten-1-ol (molar ratio) | | 5.0 | 3.0 | 3.5 | 3.1 | 3.1 | 3.1 | 0.0 | 3.0 |
| | Feed rate of 3-methyl-3-buten-1-ol (g/hr) | | 75.9 | 78.0 | 74.2 | 75.1 | 75.9 | 73.4 | 75.1 | 75.1 |
| | Feed rate of water (g/hr) | | 79.4 | 49.0 | 54.0 | 48.0 | 49.0 | 47.4 | 0.0 | 47.4 |
| | Reaction temperature (° C.) | | 170 | 170 | 160 | 160 | 140 | 190 | 170 | 120 |
| | Reaction pressure (MPa) | | 0.85 | 0.82 | 0.65 | 0.66 | 0.36 | 1.10 | 0.82 | 0.20 |
| Reaction results | Conversion of 3-methyl-3-buten-1-ol (%) | | 98.2% | 98.0% | 98.7% | 99.0% | 97.0% | 99.3% | 99.0% | 93.0% |
| | Selectivity | Isoprene | 93.1% | 91.3% | 91.7% | 91.5% | 83.5% | 89.6% | 85.4% | 72.3% |
| | | Isobutylene | 1.9% | 2.1% | 2.0% | 1.7% | 1.3% | 2.5% | 2.1% | 1.1% |
| | | 2-Methyl-3-buten-2-ol | 0.6% | 0.8% | 0.6% | 0.6% | 1.4% | 0.6% | 0.8% | 0.5% |
| | | 3-Methyl-1,3-butanediol | 0.3% | 0.3% | 0.7% | 0.4% | 5.0% | 0.1% | 0.2% | 12.3% |
| | | Methyl isopropyl ketone | 0.9% | 0.8% | 0.9% | 0.7% | 0.3% | 0.9% | 0.8% | 0.5% |
| | | Isoprene dimer | 2.8% | 3.1% | 2.7% | 3.6% | 4.3% | 4.0% | 5.3% | 3.9% |

<Examples 8 to 10>

The same operations were followed, except that in the step B of Example 1, the kind of the acidic catalyst was changed as shown in Table 2. The results are shown in Table 2.

TABLE 2

| | | | Example | | | |
|---|---|---|---|---|---|---|
| | | | 8 | 9 | 10 | 11 |
| Reaction conditions | Acidic catalyst | Kind | Sulfuric acid | Boric acid | p-Toluenesulfonic acid | Methanesulfonic acid |
| | | Concentration (% by mass) | | | 1.8 | |
| | Water/3-methyl-3-buten-1-ol (molar ratio) | | | | 5.0 | |
| | Feed rate of 3-methyl-3-buten-1-ol (g/hr) | | | | 75.9 | |
| | Feed rate of water (g/hr) | | | | 79.4 | |
| | Reaction temperature (° C.) | | | | 170 | |
| | Reaction pressure (MPa) | | | | 0.85 | |
| Reaction results | Conversion of 3-methyl-3-buten-1-ol (%) | | 98.2% | 97.5% | 97.7% | 97.1% |
| | Selectivity | Isoprene | 90.9% | 90.8% | 90.3% | 90.0% |
| | | Isobutylene | 1.8% | 1.9% | 2.0% | 2.1% |
| | | 2-Methyl-3-buten-2-ol | 0.5% | 0.7% | 0.8% | 0.7% |
| | | 3-Methyl-1,3-butanediol | 0.3% | 0.3% | 0.3% | 0.4% |
| | | Methyl isopropyl ketone | 0.8% | 0.9% | 0.8% | 0.9% |
| | | Isoprene dimer | 3.9% | 4.0% | 3.9% | 4.2% |

According to the production method of the present invention, the γ,δ-unsaturated alcohol was obtained at a selectivity of 90.5% from the α-olefin and formaldehyde and purified at a distillation yield of 95.0%, and in the subsequent dehydration reaction, the conjugated diene was obtained at a selectivity of 93.1% at maximum. The total selectivity was 80.0%, and it was noted that it is possible to produce the desired conjugated diene at a high selectivity.

INDUSTRIAL APPLICABILITY

The conjugated diene obtained by the production method of the present invention is useful as raw materials of various chemical products and polymers, and the like.

The invention claimed is:

1. A method for producing a conjugated diene, the method consisting of:
   reacting an α-olefin and formaldehyde with each other to produce a reaction liquid comprising a γ,δ-unsaturated alcohol;
   washing the reaction liquid to obtain a washed reaction liquid, wherein the washing comprises contacting the reaction liquid with an alkaline aqueous solution, and wherein the washed reaction liquid comprises an upper organic layer comprising the γ,δ-unsaturated alcohol;
   separating the upper organic layer from the washed reaction liquid to obtain a separated organic layer, then;
   distilling the separated organic layer to obtain a purified γ,δ-unsaturated alcohol; then
   subjecting the γ,δ-unsaturated alcohol to a dehydration reaction at 135 to 210° C. in the presence of an aqueous solution of an acidic catalyst, to obtain a conjugated diene, and
   optionally, purifying the conjugated diene.

2. The method according to claim 1, wherein a solvent is present in the reacting of the α-olefin with the formaldehyde.

3. The method according to claim 2, wherein the solvent is an alcohol.

4. The method according to claim 1, wherein the α-olefin is isobutene, and the γ,δ-unsaturated alcohol is 3-methyl-3-buten-1-ol.

5. The method according to claim 1, wherein the dehydration reaction comprises:
   feeding the γ,δ-unsaturated alcohol and water continuously or intermittently into a reactor; and
   removing the produced conjugated diene and water continuously or intermittently from the reaction system.

6. The method according to claim 5, wherein {(feed rate of water (mol/hr))/(feed rate of γ,δ-unsaturated alcohol (mol/hr))} is from 0.5 to 12.

7. The method according to claim 1, wherein the acidic catalyst is phosphoric acid.

8. The method according to claim 1, wherein a reaction pressure in the dehydration reaction is from 0.35 to 1.6 MPa.

9. The method according to claim 1, wherein, after the washing, the washed reaction liquid is an aqueous solution having a pH of 9 to 13.

* * * * *